US010675613B2

(12) United States Patent
Van der Zon et al.

(10) Patent No.: US 10,675,613 B2
(45) Date of Patent: Jun. 9, 2020

(54) ISOMERIZATION CATALYST

(71) Applicant: SHELL OIL COMPANY, Houston, TX (US)

(72) Inventors: Monique Van der Zon, Amsterdam (NL); Vincent Rogers, Sugar Land, TX (US); Hong-Xin Li, Lansdale, PA (US); William Edward Cormier, Harleysville, PA (US); Bjorn Moden, Glen Mills, PA (US); Bart Pelgrim, Amsterdam (NL); Wiebe S. Kijlstra, Amsterdam (NL)

(73) Assignee: Shell Oil Company, Houston, TX (US)

( * ) Notice: Subject to any disclaimer, the term of this patent is extended or adjusted under 35 U.S.C. 154(b) by 88 days.

(21) Appl. No.: 15/324,016

(22) PCT Filed: Jul. 6, 2015

(86) PCT No.: PCT/EP2015/065314
§ 371 (c)(1),
(2) Date: Jan. 5, 2017

(87) PCT Pub. No.: WO2016/005312
PCT Pub. Date: Jan. 14, 2016

(65) Prior Publication Data
US 2017/0157601 A1 Jun. 8, 2017

(30) Foreign Application Priority Data
Jul. 7, 2014 (EP) ..................................... 14176034

(51) Int. Cl.
| | |
|---|---|
| *B01J 29/06* | (2006.01) |
| *B01J 29/74* | (2006.01) |
| *B01J 37/02* | (2006.01) |
| *C10G 45/64* | (2006.01) |
| *B01J 35/02* | (2006.01) |
| *B01J 37/00* | (2006.01) |
| *B01J 35/00* | (2006.01) |
| *C10G 45/62* | (2006.01) |
| *C07C 5/22* | (2006.01) |
| *C07C 5/27* | (2006.01) |
| *B01J 37/03* | (2006.01) |
| *B01J 35/10* | (2006.01) |

(52) U.S. Cl.
CPC ......... *B01J 29/7415* (2013.01); *B01J 35/002* (2013.01); *B01J 35/0006* (2013.01); *B01J 35/0013* (2013.01); *B01J 35/023* (2013.01); *B01J 37/0009* (2013.01); *B01J 37/0201* (2013.01); *B01J 37/036* (2013.01); *C07C 5/22* (2013.01); *C07C 5/222* (2013.01); *C07C 5/226* (2013.01); *C07C 5/27* (2013.01); *C07C 5/2708* (2013.01); *C10G 45/62* (2013.01); *C10G 45/64* (2013.01); *B01J 35/1023* (2013.01); *B01J 35/1038* (2013.01); *B01J 2229/18* (2013.01); *B01J 2229/186* (2013.01); *B01J 2229/20* (2013.01); *B01J 2229/42* (2013.01)

(58) Field of Classification Search
CPC ................ B01J 29/7415; B01J 2229/18; B01J 2229/186; B01J 2229/20; B01J 2229/42; B01J 35/0006; B01J 35/023; B01J 35/002; B01J 37/0009; B01J 37/0201; B01J 37/036; C07C 5/22; C07C 5/222; C07C 5/226; C07C 5/27; C07C 5/2708; C10G 45/62; C10G 45/64
USPC ........... 502/60, 63, 64, 66, 69; 585/734, 739
See application file for complete search history.

(56) References Cited

U.S. PATENT DOCUMENTS

| | | | |
|---|---|---|---|
| 5,082,988 A | 1/1992 | Holtermann | |
| 5,166,112 A * | 11/1992 | Holtermann | ......... B01J 29/7415 502/74 |
| 5,258,570 A | 11/1993 | Skeels et al. | |
| 5,328,595 A * | 7/1994 | Rainis | .................... B01J 29/064 208/135 |
| 5,364,981 A * | 11/1994 | Knifton | ................ B01J 29/7415 568/698 |
| 5,382,353 A * | 1/1995 | Mulaskey | .............. B01J 29/061 208/138 |
| 5,552,035 A * | 9/1996 | Potter | .................... B01J 20/186 208/135 |
| 5,558,851 A * | 9/1996 | Miller | .................... B01J 29/035 423/702 |
| 5,659,099 A * | 8/1997 | Skeels | ...................... B01J 29/08 585/430 |
| 6,652,735 B2 * | 11/2003 | Degnan | .................... B01J 29/80 208/111.01 |
| 2010/0168485 A1 * | 7/2010 | Deluga | .................... B01J 21/12 585/16 |
| 2011/0286914 A1 | 11/2011 | Li et al. | |
| 2013/0267744 A1 * | 10/2013 | Kim | ...................... C07C 5/2737 585/251 |

OTHER PUBLICATIONS

Majano et al., "Al—rich Zeolite Beta by seeding in the absence of organic template", Chem. Mater. 2009, 21, pp. 4184-4191.*
De Baerdemaeker et al., "Catalytic applications of OSDA-free Beta zeolite", Jpoournal of Catalysis, 308, pp. 73-81, 2013.*
SP0514 International Search Report dated Sep. 24, 2015; 4 pages.

* cited by examiner

*Primary Examiner* — Elizabeth D Wood
(74) *Attorney, Agent, or Firm* — Charles W. Stewart

(57) ABSTRACT

Paraffin isomerization catalyst comprising of from 0.01 to 5 wt. % of a Group VIII noble metal on a carrier containing alumina and zeolite beta having a silica to alumina molar ratio (SAR) of from 5 to 15 and process employing such catalyst for isomerization of a hydrocarbon feed containing paraffins having of from 4 to 8 carbon atoms.

24 Claims, No Drawings

ISOMERIZATION CATALYST

PRIORITY CLAIM

The present application is the National Stage (§ 371) of International Application No. PCT/EP2015/065314, filed Jul. 6, 2015, which claims priority from European Patent Application No. 14176034.8, filed Jul. 7, 2014 incorporated herein by reference.

FIELD OF THE INVENTION

The present invention relates to a paraffin isomerization catalyst and to a process for isomerizing a hydrocarbon feed.

BACKGROUND OF THE INVENTION

Octane number is an indication for the ignition quality of gasoline or petrol. Branched paraffins tend to have a higher octane number than linear compounds and thereby increase the quality of a feedstock of the same boiling range. Branching can be attained in various ways such as catalytic reforming, isomerization and alkylation. Isomerization involves re-arranging straight chains to their branched isomers with very little change in boiling points. Isomerization yields a product of which at least 90 wt. % boils in the boiling point range of the feed, more specifically at least 95 wt. %, most specifically at least 98 wt. %.

The article "Liquid phase hydroisomerization of n-octane over platinum-containing zeolite-based catalysts with and without binder" by Antonio de Lucas e.a. in Ind. Eng. Chem. Res., 2006, 45, 8852-8859, describes the use of zeolite beta containing catalyst for liquid phase hydroisomerization of n-octane which zeolite beta has a silicon to aluminium ratio of 13.0 which is equivalent to a silica to alumina molar ratio (SAR) of 26.0.

The article "Catalytic applications of OSDA-free Beta zeolite" by Trees de Baerdemaeker e.a. in Journal of Catalysis, 308(2013), 73-81, describes isomerization in the presence of catalyst samples consisting of template-free zeolite beta which were brought in the NH4+-form by ion exchange followed by treating with an aqueous solution of Pt(NH3)4Cl2. The platinum containing zeolite beta samples were compressed, broken up and sieved to obtain the catalyst pellets which were tested. Due to the high conversion of n-decane in the investigated temperature window, high cracking yields are expected for the catalyst pellets containing zeolite beta having a Si/Al ratio of 4.5 and 12.4 (SAR of 9 and 24.8, respectively) at conventional isomerization conditions. Acid treatment after steam dealumination as applied in the catalyst samples having a Si/Al ratio of 25.2, 36 and 55 (SAR of 50.4, 72 and 110, respectively) leads to a decrease in the number of acid sites and higher isomerization yields.

It now surprisingly has been found that the performance of zeolite beta based catalyst in isomerization can be improved by using a specific kind of carrier namely carrier containing alumina and zeolite beta which has a SAR of from 5 to 15 which zeolite beta preferably has been prepared by a specific method which does not use organic structure directing agent. It was surprisingly found that the use of such catalyst carrier increases the yield of compounds containing at least 5 carbon atoms and/or the research octane number of the product obtained. Without wishing to be bound to any theory, it is thought that the presence of alumina binder allows a relatively high amount of the platinum to deposit on alumina instead of on the zeolite which improves the distance between acid sites and metal sites. The catalyst of the present invention can use zeolite beta which has not been dealuminated.

Therefore, the present invention now relates to a paraffin isomerization catalyst comprising of from 0.01 to 5 wt. % of a Group VIII noble metal on a carrier containing alumina and zeolite beta having a silica to alumina molar ratio (SAR) of from 5 to 15.

Further, the present invention relates to a process for isomerizing a hydrocarbon feed containing paraffins having from 4 to 8 carbon atoms by contacting the feed with a catalyst according to the invention at a temperature of from 150 to 300° C. and a pressure of from 0.1 to 30 bara.

Isomerization catalyst is generally employed with saturated hydrocarbons containing of from 4 to 8 carbon atoms, including the values 4 and 8, more specifically saturated hydrocarbons containing 5 or 6 carbon atoms. The hydrocarbons preferably are normal alkanes. Examples of suitable feed hydrocarbons include (but are not limited to) normal butane, normal pentane, normal hexane, normal heptane, normal octane, cyclohexane, methylcyclopentane, cycloheptane and methylcycloheptane, generally in the presence of hydrogen.

Generally, the hydrocarbon feed consists of from 40 to 100 wt. % of paraffins having of from 4 to 8 carbon atoms, more preferably paraffins containing 5 or 6 carbon atoms. Preferably, the feed contains at least 50 wt. % of such paraffins, more specifically at least 60 wt. %, more specifically at least 70 wt. % and most specifically at least 80 wt. %.

Generally, hydrogen is mixed with the hydrocarbon feed to form a feed mixture which is contacted with the isomerization catalyst of this invention contained in an isomerization zone. The concentration of the hydrogen in the feed mixture during this contacting step can vary widely. Preferably, the hydrogen to hydrocarbon molar ratio is at least 0.01 to 1, generally between 0.01 to 1 and 5 to 1, more preferably between 0.5 to 1 and 5 to 1 and most preferably between 0.02 to 1 and 2 to 1 (mol/mol).

Generally, the saturated feed hydrocarbon and hydrogen are contacted with the catalyst, generally present in a fixed bed, at a reaction temperature of at least 150° C., generally at least 200° C., more specifically at least 220° C. It was found that the catalyst of the present invention is especially suitable for use at a temperature of at most 300° C., more specifically at most 290° C., more specifically at most 280° C., more specifically at most 270° C., most specifically at most 260° C. Generally, the weight hourly space velocity of the saturated hydrocarbon feed stream, i.e., grams of liquid feed hydrocarbon per gram of catalyst per hour, is 0.1 to 15. The reaction pressure generally is within the range of 1 bara to 25 bara in the isomerization zone, more specifically of from 5 to 20 bara. The gas hourly space velocity of the hydrogen feed stream is generally 10-2,000 l hydrogen per l catalyst per hour so as to give the above-recited hydrogen: hydrocarbon ratio.

The isomerization catalyst of the present invention comprises a specific zeolite beta having a silica-to-alumina molar ratio (SAR) ranging from 5 and 15, preferably from 5 to 12, more specifically from 5 to 11.

The catalyst of the present invention does not need to contain chloride more especially does not need to contain any halogen. Therefore, the catalyst of the present invention preferably does not contain chloride more especially is free from halogen.

The zeolite beta for use in the catalyst of the present invention preferably does not contain organic structure directing agent. The latter means that the beta zeolite has been manufactured without the direct use of organic structure directing agent (SDA) during synthesis. However, it is appreciated that when a seeding material is used, such as a pure beta zeolite, the seeding material may have been made with or without an SDA. Thus, this term refers to fact that the resulting beta product has never been in direct contact with an organic structure directing agent (SDA) during any processing step, but that a seed material may have been made using an SDA, providing, at most, residual or secondary contact with the pore structure. The SDAs typically used to prepare beta zeolite (such as tetraethylammonium hydroxide and dibenzyl-dimethylammonium hydroxide) are not only expensive, but they inevitably are encapsulated in the zeolitic framework, such that a removal step, e.g. heat treating, is required for their removal. By avoiding the use of an organic template, the resulting beta zeolite does not have unwanted organic materials in the crystalline material. As a result, one or more post-synthetic treatments such as calcination for removing SDAs from the crystallized material is unnecessary. In addition, when organic SDAs are used to prepare beta zeolite, high silica products are typically obtained. For example, the typical SAR of synthetic beta zeolite prepared with the help of SDA is over 20, often over 40.

The present invention preferably comprises zeolite beta which has been prepared by a process which comprises
(a) mixing and stirring an alkali oxide source, an aluminum oxide source, a silicon dioxide source and water to synthesize an initial aluminosilicate gel having the following mole ratio of raw materials:
$SiO_2/Al_2O_3$=15-45, $Na_2O/SiO_2$=0.20-0.50, $H_2O/SiO_2$=4-50,
(b) adding zeolite crystal seed and allowing the mixture to crystallize at elevated temperature to obtain zeolite beta crystals having a silica to alumina molar ratio (SAR) of from 5 to 15. Preferably, the mixture is allowed to crystallize at a temperature of from 100 to 180° C. during of from 12 to 24 hours. A zeolite beta which preferably is used has been described in detail in US-A-2011/0286914.

Zeolite beta is defined and described in "Atlas of Zeolite Framework Types," ed. Baerlocher et al., Sixth Revised Edition (Elsevier 2007).

In a preferred embodiment, the zeolite beta has a volume average crystal size as determined by scanning electron microscopy of from 10 to 1000 nanometer, more especially of from 50 to 500 nanometers. Its surface area preferably is of from 400 to 800 m$^2$/g, more specifically of from 550 to 750 m$^2$/g as measured by the B.E.T. method according to ASTM test D3663-03. The micropore volume preferably is of from 0.10 to 0.40 cc/g, more specifically of from 0.15 to 0.30 cc/g as determined by ASTM test D4365-95.

The catalyst carrier for use in the present invention preferably comprises of from 50 to 98% the zeolite beta for use in the present invention. More preferably, the carrier comprises at least 60 wt. %, more specifically at least 70 wt. % of such zeolite beta. The carrier preferably comprises at most 95 wt. %, more preferably at most 90 wt. % of such zeolite beta.

The catalyst carrier can contain further zeolites but preferably consists of the zeolite beta and alumina binder.

The alumina binder generally is present in an amount of from 2 to 50 wt. % based on carrier, more specifically of from 2 to 40 wt. %, more specifically of from 5 to 30 wt. %, more specifically of from 10 to 30 wt. %, most specifically of from 10 to 25 wt. %. The binder is alumina optionally in combination with other compounds such as silica, alumina, titania, zirconia, ceria and/or gallia. Preferably, the inorganic binder consists of alumina with up to 50 wt. % of other compounds, more specifically up to 20 wt. %, more specifically up to 10 wt. %, most specifically up to 5 wt. %. Preferably, the inorganic binder consists of alumina.

In the present invention the alumina to be used as inorganic binder may originate from any source. Preferably, the binder is boehmite such as the Catapal or Pural range available from Sasol.

The present invention further relates to a process for preparing an isomerization catalyst according to the invention which process comprises (a) mixing alumina and zeolite beta having a SAR of from 5 to 15, extruding the mixture obtained and optionally drying and calcining the extrudates obtained and (b) impregnating the extrudates obtained in step (b) with a platinum containing solution followed by drying and optionally calcining the impregnated extrudates.

The impregnating solution of process step (b) preferably is an aqueous solution comprising one or more platinum chloride salts more specifically salts according to the general formula $X_nPtCl_m$ in which X is a cation, n is an integer of from 1 to 6, preferably of from 2 to 4, most preferably 2, and m is an integer of from 4 to 8, most preferably 6. X preferably is selected from the group consisting of ammonium and hydrogen. Most preferably, the impregnating solution comprises hexachloroplatinic acid.

Typically, the zeolite beta and binder are in the form of a powder and are mixed with water, and if desired or necessary, other chemical aids such as peptizing agents, flocculating agents, binders or other compounds may be added, to form a mixture or paste that may be formed into an agglomerate or shaped particle. It can be desirable to extrude the mixture to form extrudates of any one or more of various shapes such as cylinders and trilobes having nominal sizes such as ¹⁄₁₆ inch, ⅛ inch and ³⁄₁₆ inch.

The agglomerates or shaped particles can be dried under standard drying conditions that can include a drying temperature in the range of from 50 to 200° C., preferably, from 75 to 175° C., and more preferably, from 90 to 150° C. After drying, the shaped carrier particle generally is calcined under standard calcination conditions that include a calcination temperature in the range of from 250 to 900° C., preferably, from 300 to 800° C., and, most preferably, from 350 to 600° C.

The catalyst of the present invention comprises a Group VIII noble metal. The noble metal preferably is platinum and/or palladium, more preferably is platinum. The amount of the Group VIII noble metal preferably is of from 0.1 to 3 wt. %.

The noble metal is preferably incorporated in the carrier by impregnation, more specifically by pore volume impregnation. For this, the carrier preferably is impregnated with a noble metal containing solution which is similar to the pore volume of the carrier to obtain the impregnated catalyst composition. Preferably, a platinum-containing solution is used. Suitably, the platinum-containing solution has a pH-value in the range of from 0 to 5, more preferably in the range of from 0 to 4, more preferably in the range of from 0 to 3, more preferably in the range of from 0 to 2 containing a platinum containing compound such as hexachloroplatinic acid. Suitably, the impregnation is carried out at a temperature in the range of from 5 to 60° C., preferably at a temperature in the range of from 15 to 30° C. Suitably, the impregnation is carried out for a period of 30 minutes to 2 hours, preferably 45 minutes to 1.5 hours, although also longer periods of time can be used.

Preferably, the impregnated catalyst composition is subsequently calcined. The calcination can be carried out at the location where manufacture took place or alternatively the impregnated catalyst composition is transferred to the location at which it is to be used. Suitably, calcination of the impregnated carrier is carried out at a temperature in the range of from 300 to 650° C., preferably in the range of from 450 to 550° C. The period of time during which calcination is carried out will not be critical. Suitably, it can be carried out for a period of 30 minutes to 3 hours, preferably 45 minutes to 1.5 hours, although also longer periods of time can be used.

The catalyst is generally reduced before use. This is achieved by contacting the calcined catalyst with hydrogen at elevated temperature and pressure such as a temperature in the range of from 150 to 700° C. and a pressure in the range of from 2 to 40 bara.

The following examples are presented to further illustrate the present invention and are not to be construed as unduly limiting the scope of the present invention.

EXAMPLE 1—SYNTHESIS OF BETA ZEOLITE CONTAINING CATALYST

Water, NaOH (50%) and sodium aluminate (23.5% $Al_2O_3$, 19.6% $Na_2O$) were mixed together. Silica gel (available from PQ Corporation) was added to the solution and mixed vigorously for 1 hour. Finally, commercially available zeolite beta (available from Zeolyst International) in the amount of 10 wt. % with respect to the silica content of the slurry was added to the mixture and stirred for 24 hours. The gel had the following molar composition:

20.0 $SiO_2$:1.0 $Al_2O_3$:6.0 $Na_2O$:400$H_2O$

The gel was loaded into a 2-liter Parr autoclave and heated to 125° C. and maintained at that temperature for 48 hours while stirring at 175 rpm. After cooling, the product was recovered by filtration and washing. To remove residual sodium, the solid was slurried in a 3.6 M $NH_4NO_3$ solution and stirred at 90° C. for 2 hours. This $NH_4NO_3$ exchange process was repeated twice. After filtering, washing, and drying, the final product had silica-to-alumina ratio (SAR) of 9.8. The BET surface area of the product was 668 m$^2$/g and micropore volume was 0.23 cc/g.

The zeolite beta obtained was mixed with alumina binder (Sasol Pural SB1) in a weight ratio of 80:20 and 1.5 wt. % of nitric acid and 0.3 wt. % Superfloc N. The mixture had a loss on ignition of 53%. This mixture was extruded to obtain 1.4 mm diameter extrudates, dried for 2 hours at 140° C. and calcined for 2 hours at 500° C. The calcined extrudates were impregnated by pore volume impregnation with hexachloroplatinic acid solution and subsequently dried at 140° C. and calcined at 450° C. The final catalyst contained 0.3 wt. % of platinum, calculated as metal and had a compacted bulk density of 0.3 kg/l.

EXAMPLE 2—ISOMERIZATION PROCESS

This example illustrates the use of a catalyst prepared as described in Example 1 (Catalyst 1) in the isomerization of a mixture of n-pentane, n-heptane and cyclohexane.

For comparison, we also tested a catalyst containing 0.3 wt. % of platinum, calculated as metal, on extrudates comprising 20 wt. % alumina binder and 80 wt. % zeolite beta having a SAR of 25 and having a compacted bulk density of 0.48 kg/l (Catalyst A).

We further tested a comparative catalyst containing 0.3 wt. % of platinum, calculated as metal, on extrudates comprising 20 wt. % alumina binder and 80 wt. % zeolite beta having a SAR of 18 and a surface area of 675 m$^2$/g (Catalyst B).

Each of the catalysts were dried at 200° C. and reduced with hydrogen at 10 bara and 300° C. and tested on a feedstock of 60 wt % n-O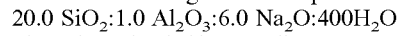$_5$, 35 wt % n-$C_6$ and 5 wt % cyclo-$C_6$.

The testing was carried out at liquid hourly space velocity of 1.90 cc feed/cc catalyst/hour, while the flow of the hydrogen gas stream was maintained to provide a ratio of hydrogen to feed of 1.2:1 (volume hydrogen on volume feed). The isomerization product was analyzed by means of a gas chromatograph.

The octanetonneyield is the calculated product yield times the calculated octane number. The octanetonneyield for the above catalysts at various temperatures are shown in Table 1 below.

TABLE 1

| Octane per tonne yield | Catalyst A | Catalyst B | Catalyst 1 |
|---|---|---|---|
| 235° C. | 6500 | 6750 | 7000 |
| 250° C. | 7400 | 7500 | 7600 |

That which is claimed is:

1. A paraffin isomerization catalyst comprising: from 0.01 to 5 wt. % of a Group VIII noble metal on a carrier containing alumina and zeolite beta that does not contain an organic structure directing agent and having a silica to alumina molar ratio (SAR) of from 5 to 15.

2. The paraffin isomerization catalyst according to claim 1, wherein the Group VIII noble metal is platinum which is present in an amount of from 0.1 to 3 wt. %.

3. The paraffin isomerization catalyst according to claim 1, wherein the carrier comprises of from 60 to 95 wt. % of the zeolite beta.

4. The paraffin isomerization catalyst according to claim 1, wherein the average crystal size of the zeolite beta as determined by scanning electron microscopy is of from 50 to 500 nanometers.

5. A paraffin isomerization catalyst, comprising a Group VIII noble metal impregnated onto a carrier comprising alumina and zeolite beta, wherein the zeolite beta is prepared by a process which comprises
   (a) mixing and stirring an alkali oxide source, an aluminum oxide source, a silicon dioxide source and water without addition of an organic structure directing agent (SDA) to provide an aluminosilicate synthesis gel having the following mole ratio of raw materials: $SiO_2/Al_2O_3$=15-45, $Na_2O/SiO_2$=0.20-0.50, $H_2O/SiO_2$=4-50; and
   (b) adding zeolite crystal seed and allowing the aluminosilicate synthesis gel to crystallize at elevated temperature to obtain the zeolite beta crystals having a silica to alumina molar ratio (SAR) of from 5 to 15.

6. The paraffin isomerization catalyst according to claim 5 wherein the process comprises allowing the aluminosilicate synthesis gel to crystallize in step (b) at a temperature of from 100 to 180° C. during from 12 to 24 hours.

7. The paraffin isomerization catalyst according to claim 1, wherein the zeolite beta has a SAR of from 5 to 12.

8. A process for preparing an isomerization catalyst according to claim 1, which process comprises (a) mixing alumina and zeolite beta, having a SAR of from 5 to 15 and made without the direct use of an organic structure directing agent (SDA) during its synthesis, to yield a mixture; (b) extruding the mixture obtained in step (a) to yield extrudates; (c) optionally drying and calcining the extrudates obtained in step (b); and (d) impregnating the extrudates obtained in step (b) or in step (c) with a platinum containing solution to provide impregnated extrudates followed by drying and optionally calcining the impregnated extrudates.

9. The process according to claim 8, in which the platinum containing solution is an aqueous solution comprising hexachloroplatinic acid.

10. The process for isomerizing a hydrocarbon feed containing paraffins having of from 4 to 8 carbon atoms by contacting the feed with a catalyst according to claim 1 at a temperature of from 150 to 300° C. and a pressure of from 0.1 to 30 bara.

11. A paraffin isomerization catalyst, comprising: a formed and calcined carrier comprising from 2 to 50 wt. % alumina and from 50 to 98 wt. % zeolite beta that does not contain an organic structure directing agent and having a silica-to-alumina molar ratio (SAR) in the range of from 5 to 12, wherein said formed and calcined carrier is impregnated with an amount of Group VIII noble metal to provide from 0.01 to 5 wt. % said Group VIII noble metal on said formed and calcined carrier.

12. The paraffin isomerization catalyst according to claim 11, wherein the Group VIII noble metal is platinum which is present in an amount of from 0.1 to 3 wt. %.

13. The paraffin isomerization catalyst according to claim 11, wherein the carrier comprises of from 60 to 95 wt. % of the zeolite beta.

14. The paraffin isomerization catalyst according to claim 11, wherein the average crystal size of the zeolite beta as determined by scanning electron microscopy is of from 50 to 500 nanometers.

15. A paraffin isomerization catalyst, comprising a Group VIII noble metal impregnated onto a carrier comprising alumina and zeolite beta, wherein the zeolite beta is prepared by a process which comprises:
(a) mixing and stirring an alkali oxide source, an aluminum oxide source, a silicon dioxide source and water without addition of an organic structure directing agent (SDA) to provide an aluminosilicate synthesis gel having the following mole ratio of raw materials: $SiO_2/Al_2O_3$=15-45, $Na_2O/SiO_2$=0.20-0.50, $H_2O/SiO_2$=4-50; and (b) adding zeolite crystal seed and allowing the aluminosilicate synthesis gel to crystallize at elevated temperature to obtain the zeolite beta crystals having a silica to alumina molar ratio (SAR) of from 5 to 12.

16. The paraffin isomerization catalyst according to claim 15, wherein the process comprises allowing the aluminosilicate synthesis gel to crystallize in step (b) at a temperature of from 100 to 180° C. during from 12 to 24 hours.

17. The paraffin isomerization catalyst according to claim 1, wherein the zeolite beta has a SAR of from 5 to 11.

18. The process for isomerizing a hydrocarbon feed containing paraffins having of from 4 to 8 carbon atoms by contacting the feed with a catalyst according to claim 2 at a temperature of from 150 to 300° C. and a pressure of from 0.1 to 30 bara.

19. The process for isomerizing a hydrocarbon feed containing paraffins having of from 4 to 8 carbon atoms by contacting the feed with a catalyst according to claim 3 at a temperature of from 150 to 300° C. and a pressure of from 0.1 to 30 bara.

20. The process for isomerizing a hydrocarbon feed containing paraffins having of from 4 to 8 carbon atoms by contacting the feed with a catalyst according to claim 4 at a temperature of from 150 to 300° C. and a pressure of from 0.1 to 30 bara.

21. The process for isomerizing a hydrocarbon feed containing paraffins having of from 4 to 8 carbon atoms by contacting the feed with a catalyst according to claim 11 at a temperature of from 150 to 300° C. and a pressure of from 0.1 to 30 bara.

22. The process for isomerizing a hydrocarbon feed containing paraffins having of from 4 to 8 carbon atoms by contacting the feed with a catalyst according to claim 12 at a temperature of from 150 to 300° C. and a pressure of from 0.1 to 30 bara.

23. The process for isomerizing a hydrocarbon feed containing paraffins having of from 4 to 8 carbon atoms by contacting the feed with a catalyst according to claim 13 at a temperature of from 150 to 300° C. and a pressure of from 0.1 to 30 bara.

24. The process for isomerizing a hydrocarbon feed containing paraffins having of from 4 to 8 carbon atoms by contacting the feed with a catalyst according to claim 14 at a temperature of from 150 to 300° C. and a pressure of from 0.1 to 30 bara.

* * * * *